(12) United States Patent
Igarashi et al.

(10) Patent No.: US 11,004,195 B2
(45) Date of Patent: May 11, 2021

(54) IMAGE PROCESSING DEVICE, IMAGE PROCESSING METHOD, PROGRAM, AND RECORDING MEDIUM

(71) Applicant: University of Tokyo, Tokyo (JP)

(72) Inventors: Takeo Igarashi, Tokyo (JP); Taichi Kin, Tokyo (JP)

(73) Assignee: University of Tokyo, Tokyo (JP)

( * ) Notice: Subject to any disclaimer, the term of this patent is extended or adjusted under 35 U.S.C. 154(b) by 513 days.

(21) Appl. No.: 15/737,019

(22) PCT Filed: Jun. 16, 2016

(86) PCT No.: PCT/JP2016/067971
§ 371 (c)(1),
(2) Date: Apr. 5, 2018

(87) PCT Pub. No.: WO2016/204241
PCT Pub. Date: Dec. 22, 2016

(65) Prior Publication Data
US 2018/0211382 A1 Jul. 26, 2018

(30) Foreign Application Priority Data
Jun. 19, 2015 (JP) .............................. JP2015-123629

(51) Int. Cl.
*G06T 7/00* (2017.01)
*G06T 15/00* (2011.01)
(Continued)

(52) U.S. Cl.
CPC .............. *G06T 7/0012* (2013.01); *G06T 7/11* (2017.01); *G06T 7/136* (2017.01); *G06T 15/00* (2013.01);
(Continued)

(58) Field of Classification Search
CPC ......... G06T 7/0012; G06T 7/136; G06T 7/11; G06T 15/00; G06T 15/08
See application file for complete search history.

(56) References Cited

U.S. PATENT DOCUMENTS

2006/0050966 A1    3/2006  Nishimura et al.
2008/0119713 A1*   5/2008  Le Nezet ........... A61B 5/02007
                                                      600/407
(Continued)

FOREIGN PATENT DOCUMENTS

JP    2004-181096    7/2004
JP    2007-265331    10/2007
WO    WO 2015053319  4/2015

OTHER PUBLICATIONS

International Search Report; PCT/JP2016/067971; dated Sep. 20, 2016; 2 pages.
(Continued)

*Primary Examiner* — Vincent Rudolph
*Assistant Examiner* — Raphael Schwartz
(74) *Attorney, Agent, or Firm* — Fish & Richardson P.C.

(57) ABSTRACT

Provided is an image processing device including a changing unit that changes a threshold value of intensity of each of points within an image, a first display control unit that controls displaying of points including an intensity value equal to or greater than the threshold value every time the threshold value is changed by the changing unit, a receiving unit that receives designation of one or a plurality of predetermined regions within a displayed image based on an operation of a user, a fixing unit that fixes the threshold value of each of the points within the designated predetermined region as a threshold value by the changing unit at a time of designation of the predetermined region, a second display control unit that controls displaying of points including an intensity value equal to or greater than the threshold value
(Continued)

fixed by the fixing unit among the points within the predetermined region, and points including an intensity value equal to or greater than the threshold value to be changed by the changing unit among the points outside the predetermined region, in a case where there is one or the plurality of predetermined regions within the image.

16 Claims, 15 Drawing Sheets

(51) Int. Cl.
    *G06T 15/08*     (2011.01)
    *G06T 7/136*     (2017.01)
    *G06T 7/11*     (2017.01)
    *A61B 5/055*     (2006.01)
    *A61B 5/02*     (2006.01)

(52) U.S. Cl.
    CPC .......... *G06T 15/08* (2013.01); *A61B 5/02007* (2013.01); *A61B 5/055* (2013.01); *A61B 2576/00* (2013.01); *G06T 2207/30101* (2013.01)

(56) References Cited

U.S. PATENT DOCUMENTS

2009/0034812 A1\* 2/2009 Nowinski ............. A61B 5/055
    382/131
2014/0301624 A1\* 10/2014 Barckow ................ A61B 6/469
    382/131

OTHER PUBLICATIONS

Oliya Yabuta, "Adobe Photoshop CS3 Perfect Master Photoshop CS3/ Extended / CS2 / CS /7.0 Compatible Windows / Macintosh Compatible", 1st Edition, Shuwa Co. Ltd., Dec. 5, 2007.

\* cited by examiner

IMAGE PROCESSING DEVICE, IMAGE PROCESSING METHOD, PROGRAM, AND RECORDING MEDIUM

TECHNICAL FIELD

The present invention relates to an image processing device, an image processing method, a program, and a recording medium.

BACKGROUND ART

On medical scenes, there are demands for extracting a target such as a blood vessel from an examination image which is obtained using computer tomography (CT), magnetic resonance imaging (MRI), or the like. For the demands, in the related art, it is known that a user selects a predetermined region while looking at a screen and extracts a target by setting a threshold value with respect to intensity or the like for each selected predetermined region (for example, Patent Document 1).

CITATION LIST

Patent Document

Patent Document 1: Pamphlet of International Publication No. 2015-053319

SUMMARY

Technical Problem

However, according to technologies in the related art, since targets are partially different from each other in size, intensity, or the like, it has been necessary to select a predetermined region within an image many times over in accordance with the size, the intensity, or the like of the part of the targets, or to delete an unnecessary part such as clutter within the predetermined region, so that it has taken a long time to extract the targets.

Therefore, a certain aspect of the present invention aims to provide an image processing device, which is capable of reducing time for extracting a target from an image, an image processing method, a program, and a recording medium.

Solution to Problem

According to an aspect of the present invention, there is provided an image processing device including a changing unit that changes a threshold value of intensity of each of points within an image,
a first display control unit that controls displaying of points including an intensity value equal to or greater than the threshold value every time the threshold value is changed by the changing unit,
a receiving unit that receives designation of one or a plurality of predetermined regions within a displayed image based on an operation of a user,
a fixing unit that fixes the threshold value of each of the points within the designated predetermined region as a threshold value by the changing unit at a time of designation of the predetermined region, and
a second display control unit that controls displaying of points including an intensity value equal to or greater than the threshold value fixed by the fixing unit among the points within the predetermined region, and points including an intensity value equal to or greater than the threshold value to be changed by the changing unit among the points outside the predetermined region, in a case where there is one or the plurality of predetermined regions within the image.

Advantageous Effects of Invention

According to a predetermined aspect of the present invention, it is possible to properly extract a target from an image and to reduce a processing time.

DESCRIPTION OF EMBODIMENTS

Hereinafter, an embodiment of the present invention will be described in detail with reference to the accompanying drawings.

INDUSTRIAL APPLICABILITY

Embodiment

<Configuration>

Figure 1:
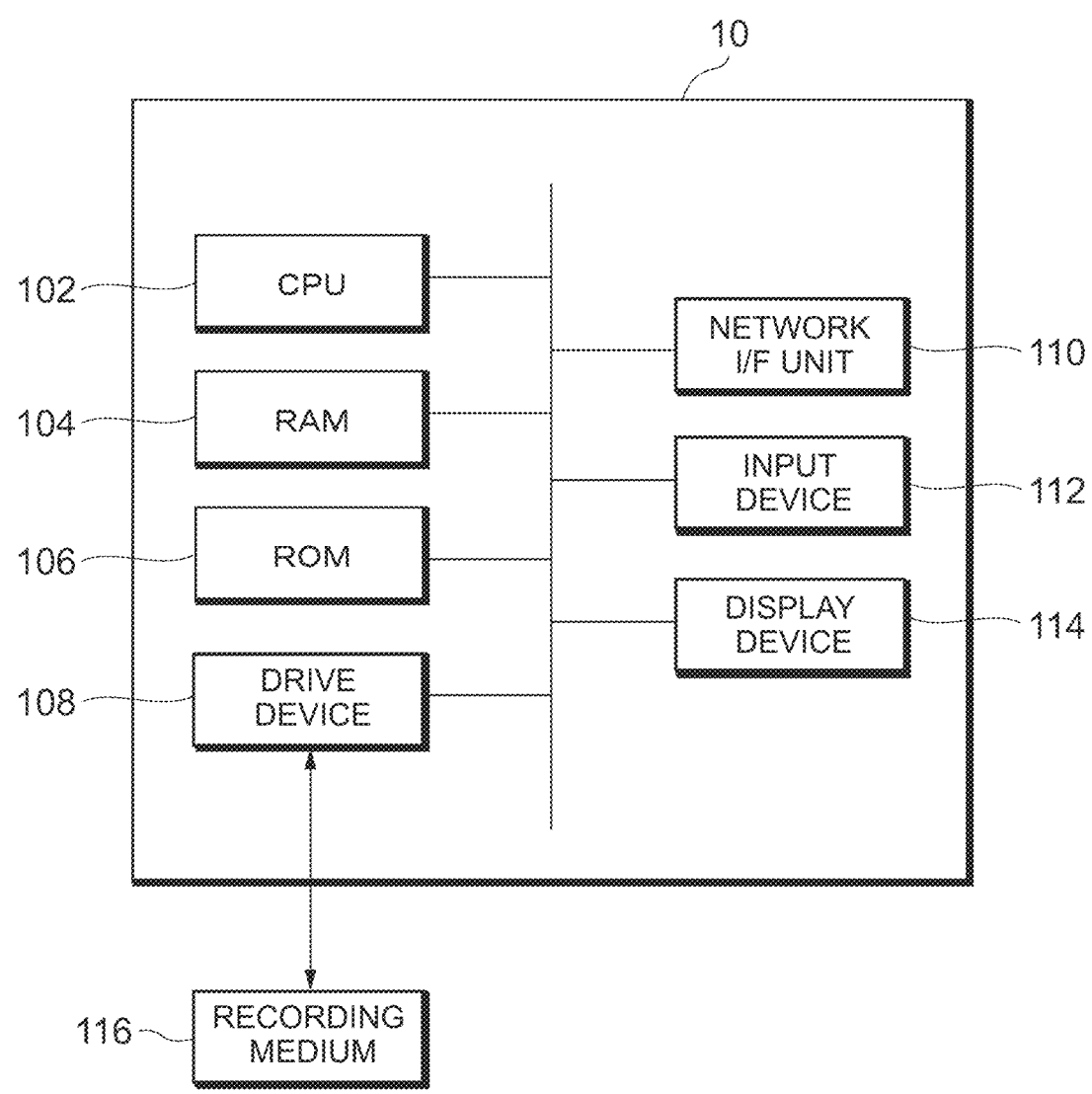
FIG. 1 is a block diagram illustrating an example of a schematic configuration of an image processing device according to an embodiment.

FIG. 1 is a block diagram illustrating an example of a schematic configuration of an image processing device 10 according to the embodiment. As illustrated in FIG. 1, the image processing device 10 has a central processing unit (CPU) 102, a random access memory (RAM) 104, a read only memory (ROM) 106, a drive device 108, a network interface (I/F) 110, an input device 112, and a display device 114. The configurations are connected to each other via a bus so as to be capable of transmitting and receiving data.

The CPU 102 is a control unit which controls each of the devices, and computes and processes data, in a computer. In addition, the CPU 102 is a computation device executing an application program which is stored in the RAM 104 or the ROM 106 and extracts a target from an image. The CPU 102 receives image data from the input device 112, the network I/F 110, or the like, computes and processes the received data, and outputs a computation result to the display device 114, a storage device, or the like.

For example, the RAM 104 is a main storage unit. The RAM 104 is a storage device storing or temporarily retaining a program or data such as an operating system (OS) which is basic software executed by the CPU 102, and application software.

For example, the ROM 106 is a storage device storing data related to the application software or the like.

The drive device 108 reads out a program or data from a recording medium 116, for example, a CD-ROM or an SD card, installs a program or data in the storage device, or downloads a program or data.

In addition, a predetermined program is stored in the recording medium 116, and the program stored in the recording medium 116 is installed in the image processing device 10 via the drive device 108. The image processing device 10 is capable of executing the installed predetermined program.

The network I/F 110 is an interface between peripherals having a communication function, and the image processing device 10. In addition, for example, the network I/F 110 is connected via a network such as a local area network (LAN) and a wide area network (WAN) established by a data transmission path such as a wire and/or a radio line.

The input device 112 has a cursor key; a keyboard including numeric input keys, various functional keys, and the like; a mouse or a slide pad for selecting a key on a display screen of the display device 114; and the like. In addition, the input device 112 is a user interface with which a user applies an operational instruction to the CPU 102 and inputs data.

The display device 114 is constituted of a liquid crystal display (LCD) or the like and performs displaying in accordance with display data input from the CPU 102. The input device 112 and the display device 114 may be provided outside the image processing device 10.

<Function>

Figure 2:
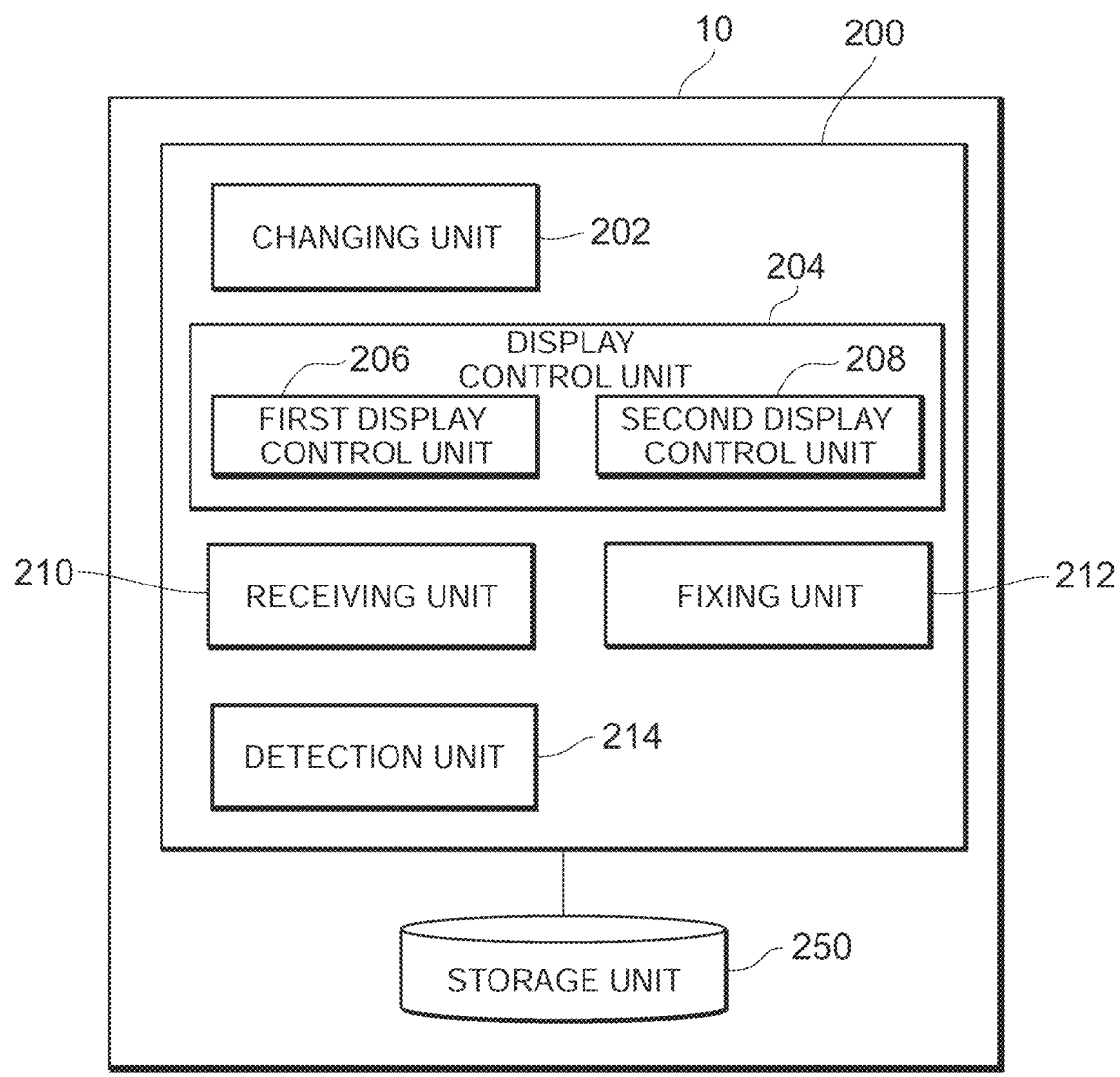
FIG. 2 is a block diagram illustrating an example of a function of the image processing device according to the embodiment.

Subsequently, a function of the image processing device 10 will be described. FIG. 2 is a block diagram illustrating an example of a function of the image processing device 10 according to the embodiment. The image processing device 10 illustrated in FIG. 2 includes a computation unit 200 and a storage unit 250. The computation unit 200 includes at least a changing unit 202, a display control unit 204, a receiving unit 210, a fixing unit 212, and a detection unit 214.

For example, the computation unit 200 illustrated in FIG. 2 is able to be realized by the CPU 102 or the RAM 104 as a working memory. The CPU 102 is capable of executing the function of each of the units inside the computation unit 200 by executing the application program for extracting a target from an image. In addition, for example, the storage unit 250 is able to be realized by the RAM 104 and/or the ROM 106.

For example, the display control unit 204 performs controlling such that the display device 114 displays an execution screen of application for extracting a target such as a blood vessel from a medical examination image. The execution screen displays a tool for changing a threshold value of intensity or the like of each of points within an image, a tool for painting a predetermined region within an image, and the like (will be described below using FIG. 3). For example, a point within an image indicates a pixel in a case of a two-dimensional image and indicates a voxel in a case of a three-dimensional image.

The changing unit 202 changes the threshold value of intensity of each of the points within an image displayed in the display device 114. The intensity of an image may be chroma, brightness, and the like. In addition, the threshold value may be a threshold value for edge detection. In regard to a change of the threshold value, the user may cause the changing unit 202 to change the threshold value by operating a slider or like for changing the threshold value displayed in the screen, or the threshold value may automatically change in order in an increment or decrement manner.

The display control unit 204 has a first display control unit 206 and a second display control unit 208. For convenience of description, the first display control unit 206 and the second display control unit 208 are separately described. However, they may be executed in one module. The first display control unit 206 performs controlling such that the display device 114 displays points including an intensity value equal to or greater than the threshold value every time the threshold value is changed by the changing unit 202.

Accordingly, the user is capable of grasping a target to be displayed at the time of the corresponding threshold value. For example, in a case where the threshold value is small, a small target having low intensity, for example, a small blood vessel is likely to be displayed. However, an artifact such as clutter is also likely to be displayed. On the other hand, in a case where the threshold value is great, an artifact such as clutter is unlikely to be displayed. However, only a target having high intensity, for example, a large blood vessel is likely to be displayed.

The receiving unit 210 receives designation of one or a plurality of predetermined regions within a displayed image based on an operation of the user. For example, an operation of the user includes a clicking operation for designating an interlink region, and a dragging operation for enlarging an interlink region. Here, it is preferable to map a simple operation of the user such as clicking and dragging with designation of the predetermined region. The interlink region is a region based on points including an intensity value equal to or greater than the threshold value by the changing unit 202. For example, the interlink region is a region in which neighbor (interlink) cells among cells having an intensity value greater than the threshold value (described below) are gathered.

The fixing unit 212 fixes the threshold value of each of the points within the designated predetermined region as a threshold value by the changing unit 202 at the time when the predetermined region has been designated. Since the threshold value of each of the points within the predetermined region is fixed, even if the changing unit 202 changes the threshold value, the predetermined region is able to be continuously displayed without being affected by the change.

In a case where there is one or the plurality of predetermined regions designated by the user within an image, the second display control unit 208 controls displaying of points including intensity equal to or greater than the threshold value fixed by the fixing unit 212 among the points within the predetermined region, and points including intensity equal to or greater than the threshold value to be changed by the changing unit 202 among the points outside the predetermined region. That is, even if the threshold value is changed, there is no change in an image within the predetermined region. It is because the predetermined region is a region designated by the user and it is preferable that the content is not changed.

In addition, the application enables the predetermined region to be more simply selected and discriminated by using a painting function. For example, in a case where the user has designated a predetermined position of a displayed image within the interlink region, the receiving unit 210 receives the interlink region as designation of the predetermined region. In this case, the second display control unit 208 may control changing of the color of the interlink region to a predetermined color and displaying the changed interlink region.

Accordingly, the user is capable of designating a region, fixing a threshold value, and discriminating the region with one click. Since the designated predetermined region need only be able to be discriminated from other regions, oblique lines or the like may be applied in addition to a change in color.

In addition, a predetermined operation at the time of a dragging operation having a position within the predetermined region as a starting position enables the changing unit 202 to change the threshold value within a predetermined range from a destination of the dragging. For example, the threshold value is subjected to an increment or a decrement by pressing down lateral arrow keys at the time of a dragging operation.

In this case, the receiving unit 210 receives a dragging operation having a location in the vicinity of the designated predetermined region as the starting position. Moreover, the receiving unit 210 may receive an interlink region, which includes a trace of the dragging operation and is displayed in accordance with a change of the threshold value within the predetermined range of the destination of the dragging based on the predetermined operation, as designation for enlarging the predetermined region. Accordingly, it is possible to easily implement enlargement of the predetermined region.

In addition, in a case where there is a neighbor point of which the threshold value is not fixed among points neighboring a point within the designated predetermined region, the fixing unit 212 may fix the threshold value of the neighbor point. Accordingly, even if the threshold value is changed, the border of the region is unlikely to be changed, and it is possible to stably provide displaying of a location in the vicinity of the border of the region.

For example, in a case where the predetermined region is displayed in the predetermined color, the detection unit 214 detects a false isosurface of which the color ought not to be changed to the predetermined color, on the border of the region of which the color is changed to the predetermined color, based on a gradient direction of the intensity of the image and a normal direction of an isosurface in the region.

The false isosurface indicates an isosurface which is not originally intended to be displayed but has been displayed due to a rapid change of the threshold value performed by the user within the region. For example, if the threshold value rapidly changes from 200 to 50 in a background region in which the intensity value is constant at approximately 100, an isosurface is generated at a location at which the intensity value does not change originally. The detection unit 214 detects the region as a false isosurface.

For example, the detection unit 214 compares the downward gradient direction of the intensity of an image and the normal direction of an isosurface on the border of a region having points including an intensity value equal to or greater than the threshold value. For example, if both the directions are directions opposite to each other, the detection unit 214 determines that the part of the isosurface is not able to correctly express the internal structure of original image data. In addition, in order to facilitate implementation, the detection unit 214 may use the downward gradient direction of a value obtained by subtracting the threshold value from the intensity value, as the gradient direction of the intensity.

The second display control unit 208 changes the color of the region detected by the detection unit 214 to a special color different from the predetermined color. Accordingly, the user is capable of easily recognizing a false isosurface. Since the false isosurface need only be able to be discriminated from other regions, the false isosurface may be able to be discriminated by hatching or the like in addition to being changed in color.

The storage unit 250 stores a program for extracting a target from an image or stores intermediate data or the like of the processing described above. The storage unit 250 may be distributed in a plurality of storage units.

As described above, for example, the user is capable of easily and properly extracting a target such as a blood vessel which the user intends to extract, by only designating a region case by case while changing the threshold value with respect to a complicated image such as a CT image and an MRI image. Consequently, it is possible to properly extract a target from an image and to reduce the processing time. Moreover, compared to technologies in the related art, it is not necessary for the user to worry about setting a proper threshold value for each designated region.

In addition, in regard to enlargement of an extraction target region, the user is capable of designating a region to be displayed while changing the threshold value on the periphery of the region intended to be enlarged. Therefore, it is possible to easily and simply enlarge an extraction target from an image.

<Application Execution Screen>

Subsequently, an example of the execution screen of application in which the present invention is implemented will be described. As an example of the image, a three-dimensional image of a head obtained through an examination such as MRI is adopted. It is postulated that the image will be referred to when a surgical operation is performed, and the extraction target is a blood vessel.

Figure 3:
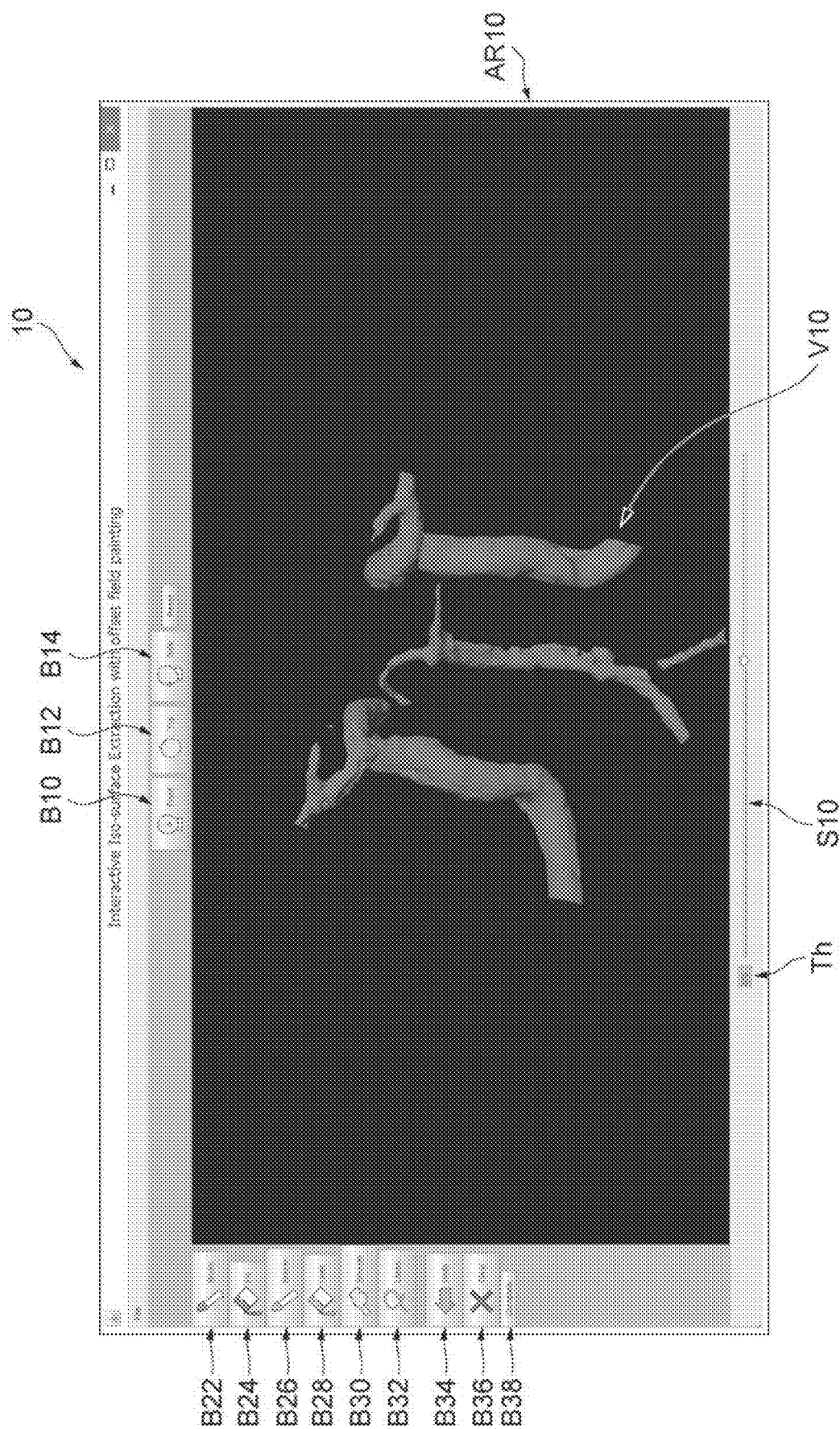
FIG. 3 is a view illustrating an example of an execution screen of application according to the embodiment.

FIG. 3 is a view illustrating an example of an execution screen of application according to the embodiment. A screen D10 illustrated in FIG. 3 includes a region AR10 displaying a three-dimensional image of the head. A blood vessel V10 is included within the three-dimensional image. In addition, the screen D10 includes buttons for executing a plurality of functions.

Buttons B10 to B14 are buttons for changing the viewpoint. The button B10 is a button for displaying a front view. The button B12 is a button for displaying a top view. The button B14 is a button for displaying a side view.

The display control unit 204 switches the viewpoint within the region AR10 based on a press-down of each of the buttons. The display control unit 204 is capable of minutely changing the viewpoint of an image in accordance with a dragging direction while a dragging operation is performed within the region AR10.

A slider S10 is a slider for changing the threshold value of intensity of each of the points within an image. Hereinafter, the threshold value changed by the slider will also be referred to as a first threshold value. In the example of the screen illustrated in FIG. 3, the first threshold value decreases by sliding a knob portion to the left, and the first threshold value increases by sliding the knob portion to the right. A first threshold value Th is displayed in accordance with the position of the knob portion in the slider S10. In the example illustrated in FIG. 3, a current first threshold value Th is "470". The changing unit 202 changes the first threshold value in accordance with a change of the position of the knob portion through an operation of the user.

In an image within the region AR10, the size, the position, and the like of the blood vessel V10 including an isosurface change due to a change of the first threshold value. The first display control unit 206 controls displaying of the blood vessel V10 including intensity equal to or greater than the first threshold value in accordance with a change of the first threshold value.

Subsequently, the painting function for facilitating designation of a blood vessel which is an extraction target and facilitating discrimination of a result of an extraction target will be described.

A button B24 is a button indicating a filling tool for the user designating or filling the predetermined region. The designated predetermined region indicates a target which the user intends to extract. In addition, if a click is detected after the button B24 is pressed, the receiving unit 210 receives the interlink region including the clicked position as designation of the predetermined region. For example, the interlink region is changed to the predetermined color. For example, the predetermined color is a reddish color. Accordingly, the designated region is easily discriminated.

A button B22 is a button indicating a brushing tool for enlarging a designated blood vessel. If a dragging operation is detected after the button B22 is pressed, it is possible to enlarge the blood vessel including a trace of a dragging operation along the trace. The receiving unit 210 receives the interlink region including the trace of a dragging operation as designation of the extraction target region by receiving a dragging operation after the button B22 is pressed down. Accordingly, the user is capable of easily enlarging the region by using a dragging operation. In this case, it is possible to change the threshold value within the predetermined range from a brushing destination (destination of the dragging). Hereinafter, the threshold value will also be referred to as a second threshold value.

A button B26 is a button indicating an eraser tool for deleting the predetermined region of the extraction target. If a dragging operation is detected after the button B26 is pressed, the predetermined range including the trace is erased along the trace of the dragging. Accordingly, it is possible to erase a part of the extraction target region intended to be erased.

A button B28 is a button indicating an unfilling tool for canceling designation or filling of the predetermined region. If a click is detected within the region designated by the button B24 after the button B28 is pressed, designation of the region is canceled.

A button B30 is a button indicating a smoothing tool for smoothing the border portion of the predetermined region. After the button B30 is pressed, Laplacian smoothing is applied to the periphery of the clicked position. For example, the tool is useful for alleviating discontinuity of the threshold value which appears on a brushing border.

A button B32 is a button indicating a lasso tool for designating an arbitrary region. If a dragging operation of forming an interlink region is detected after the button B32 is pressed, the inside of the trace of the dragging is selected.

A button B34 is a button indicating an undoing tool for returning to the immediately preceding operation. If the button B34 is pressed, displaying returns to the status after the immediately preceding operation has been executed.

A button B36 is a button indicating a clear tool for erasing a selected target within a region. If the button B36 is pressed in a state where an interlink region is selected by pressing down the button B32, the target within the interlink region is erased.

A button B38 is a button indicating a completion tool for confirming an image including an isosurface intended to be extracted. If the button B38 is pressed, the extraction target within the region AR10 is fixed.

<Overview of Processing Procedure of Proposal Technique>

Figure 4:
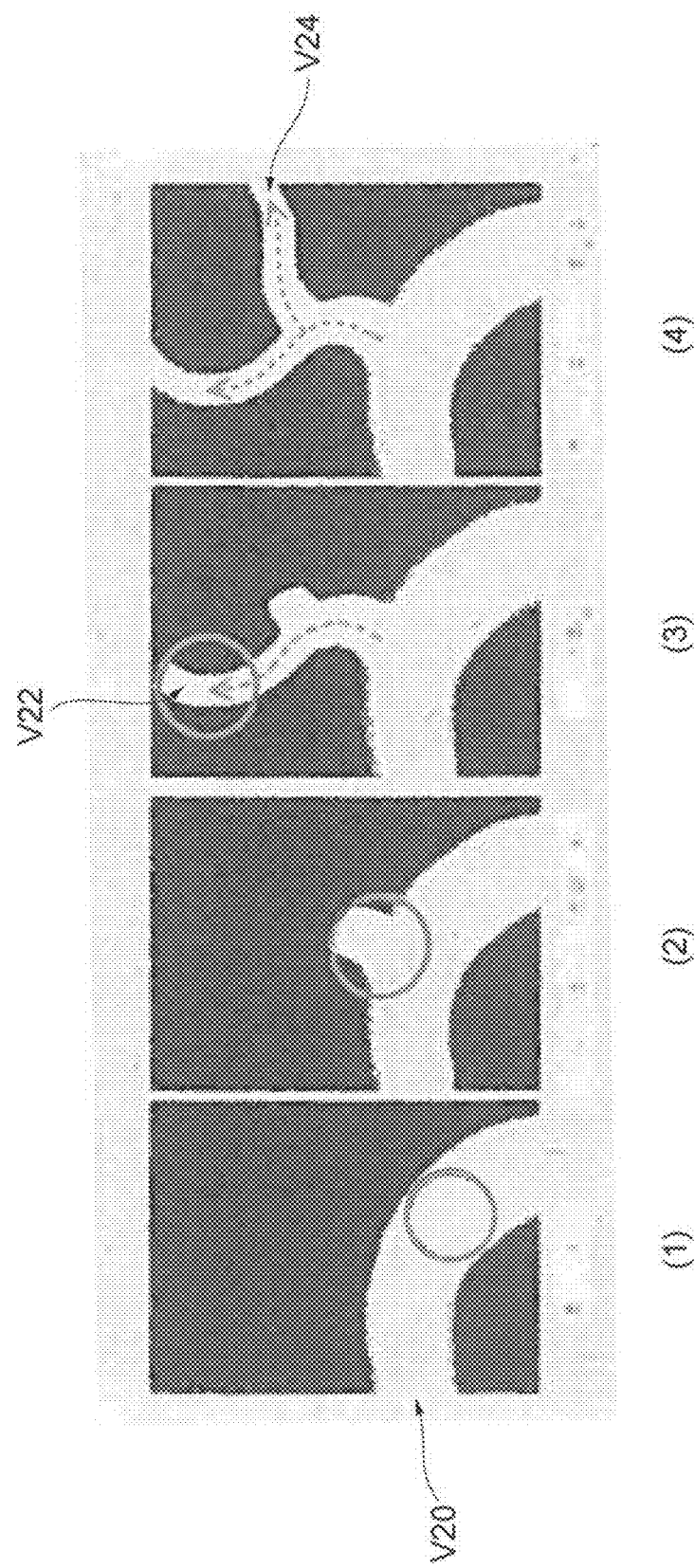
FIG. 4 is a view for describing an overview of a processing procedure of the image processing device according to the embodiment.

FIG. 4 is a view for describing an overview of a processing procedure of the image processing device 10 according to the embodiment. In the example illustrated in FIG. 4, a target is extracted in the following procedure.

(1) Designation of Predetermined Region at High Threshold Value

If a location within the predetermined region of an interlink region V20 is clicked after the button B24 is pressed in a state where the first threshold value is set to be high (significant), the interlink region V20 including the clicked position is painted with the predetermined color.

(2) Starting of Region Enlargement

If a dragging operation is detected while having a position within the interlink region or within the painted region as the starting position after the button B22 is pressed, a region including points of which the intensity value is greater than the second threshold value appears along the trace of the dragging, and the region is designated. In regard to a position of dragging, it is preferable for the user to grasp the place where the target is present by minutely changing the first threshold value in advance.

(3) Region Enlargement (Stage 1)

If a dragging operation continues and the second threshold value is changed, an interlink region V22 including the trace of the dragging and including points of which the intensity value is equal to or greater than the second threshold value is designated. In this case, it is preferable to display the interlink region V22 by minutely changing the second threshold value. In a case where there is no interlink region at the destination of the dragging, no region is designated.

(4) Region Enlargement (Stage 2)

Moreover, a dragging operation is detected while having a position within the interlink region V22 as the starting position, a region V24 including the trace is designated along the trace of the dragging. In regard to enlargement through a dragging operation, there is no particular limitation or the like for the number of times thereof.

Accordingly, it is possible to easily extract a target by using the painting function based on the clicking operation and the dragging operation.

<Relationship between Intensity Value and Threshold Value>

Figure 5:
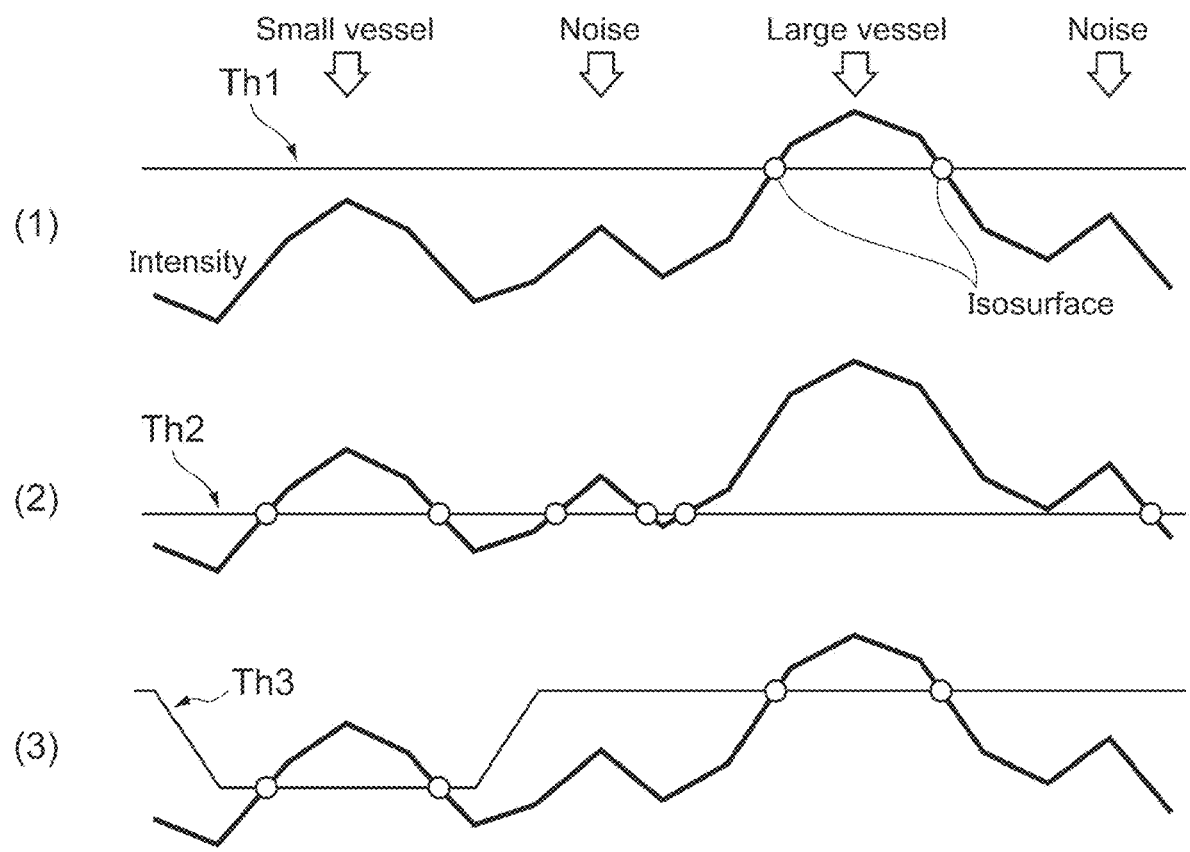
FIG. 5 is a view illustrating a relationship between an intensity value and a threshold value.

FIG. 5 is a view illustrating a relationship between an intensity value and a threshold value. The way how an isosurface appears (is displayed) will be described by using an example of a certain cross section illustrated in FIG. 5.

(1) High Threshold Value

In a case where a high threshold value Th1 is set, an intensity value which coincides with the threshold value Th1 appears as an isosurface. Large blood vessels including an intensity value equal to or greater than the intensity value are displayed. Consequently, only large blood vessels are extracted, and small blood vessels are unlikely to be extracted.

(2) Low Threshold Value

In a case where a low threshold value Th2 is set, an intensity value which coincides with the threshold value Th2 appears as an isosurface. Small blood vessels equal to or greater than the intensity value, noise, and large blood vessels are displayed. Consequently, small blood vessels are able to be displayed. However, much noise is also displayed at the same time.

(3) Threshold value in Proposal Technique

As indicated in a threshold value Th3, since the threshold value is able to be easily and appropriately set at an arbitrary place, it is possible to display blood vessels only. For example, large blood vessels are designated through a clicking operation illustrated in (1) of FIG. 4, and small blood vessels are designated through a dragging operation illustrated in (2) to (4) of FIG. 4.

<Designation Processing of Target Region>

Subsequently, using FIGS. 6A to 6H, designation processing of a target region will be described in detail. Here, a region of blood vessels becomes a target region.

Figure 6A:
FIG. 6A is a view for describing designation processing of a target region (stage 1).

In the example illustrated in FIG. 6A, the changing unit 202 has set the first threshold value to 250 (low value) based on an operation of the user. Since the first threshold value is low, many blood vessels and clutter are displayed within the image.

Figure 6B:
FIG. 6B is a view for describing the designation processing of a target region (stage 2).

In the example illustrated in FIG. 6B, the changing unit 202 has set the first threshold value to 500 (high value) based on an operation of the user. Since the first threshold value is high, large blood vessels are displayed, and small blood vessels and the like are not displayed within the image. In this manner, the user is capable of grasping a displaying condition of blood vessels in accordance with a change of the first threshold value by appropriately changing the first threshold value using the slider S10 illustrated in FIG. 3.

Figure 6C:
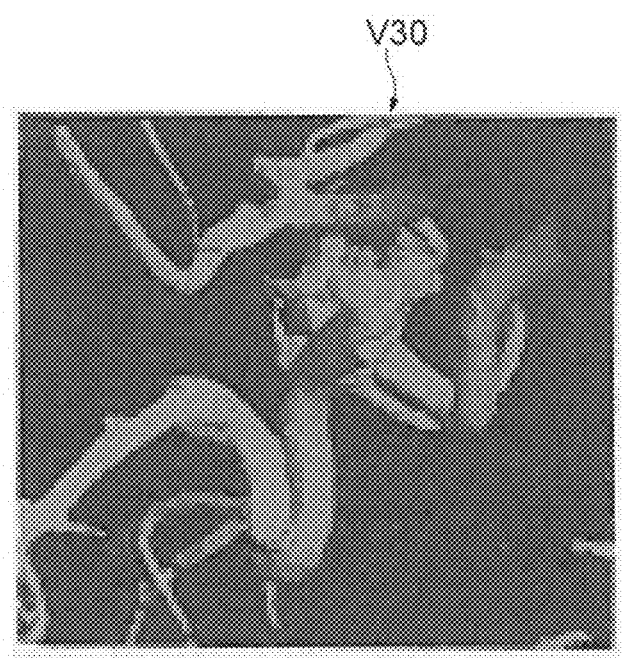
FIG. 6C is a view for describing the designation processing of a target region (stage 3).

In FIG. 6C, when the first threshold value is 500, the user has pressed the button B24 and has clicked a location within an interlink region V30 of a blood vessel. The receiving unit 210 receives designation of the inside of the interlink region V30 of the blood vessel based on the operation, and the second display control unit 208 changes the color of the interlink region V30 to the predetermined color. In this case, the fixing unit 212 fixes the threshold value within the interlink region V30 to 500.

Accordingly, even if the first threshold value is changed by the user using the slider S10 after the threshold value is fixed, since the threshold value of the interlink region V30 is fixed, there is no change in displaying of the interlink region V30.

Figure 6D:
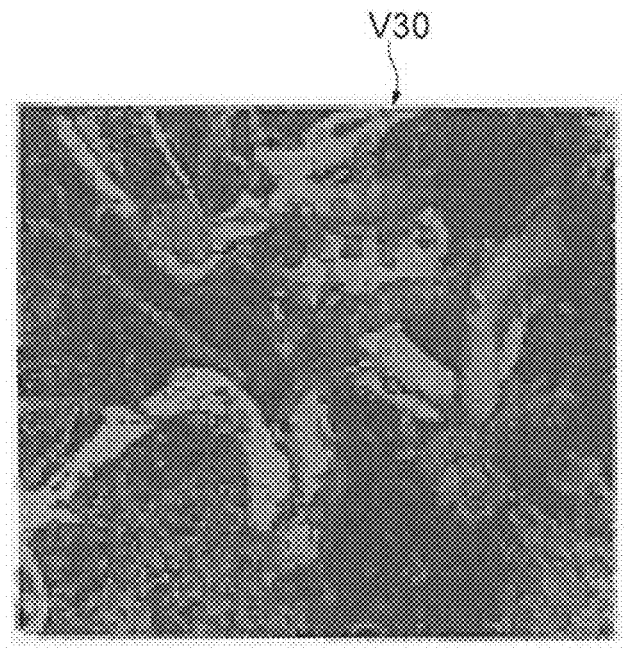
FIG. 6D is a view for describing the designation processing of a target region (stage 4).

In FIG. 6D, the user has lowered the first threshold value by using the slider S10 so as to return to 250 in order to grasp the structure of the blood vessel in more detail. In this case, since the interlink region V30 has a color different from those of other regions, the interlink region V30 is likely to be discriminated. In addition, the user is capable of grasping an overview of the structure of the blood vessel.

Figure 6E:
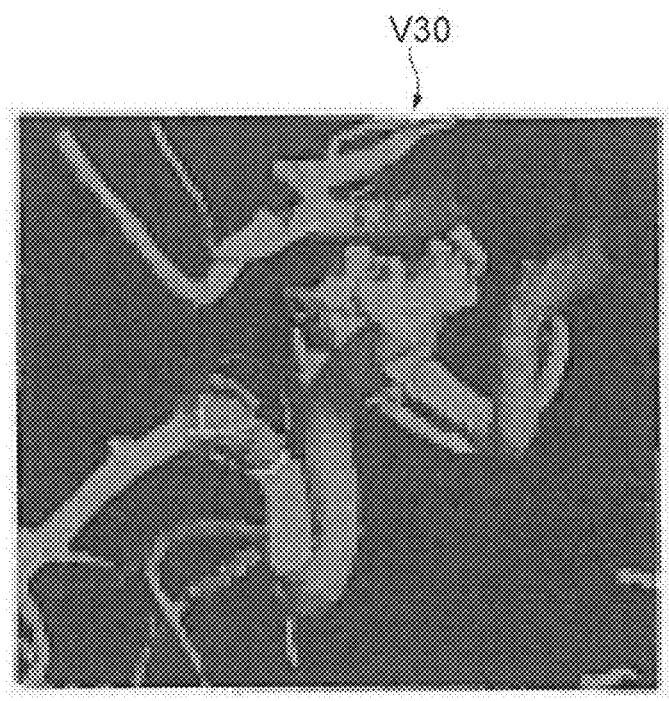
FIG. 6E is a view for describing the designation processing of a target region (stage 5).

In FIG. 6E, the user causes the first threshold value to return to 500, presses the button B22 illustrated in FIG. 3, and enlarges the blood vessel. Here, a small blood vessel of a part which has been grasped in FIG. 6D and is surrounded by a circle illustrated in FIG. 6E is enlarged.

The user starts a dragging operation from the starting position within the interlink region V30. Moreover, the user lowers the second threshold value by performing the predetermined operation. Accordingly, the second threshold value within the predetermined range from the destination of the dragging is lowered, and small blood vessels are displayed. For example, the second threshold value is changed to 250 based on the predetermined operation. For example, as the predetermined operation, the left arrow key in the keyboard is pressed down. In addition, the right arrow key in the keyboard may be allocated as a key for increasing the second threshold value within the predetermined range from the destination of the dragging.

Consequently, the user is capable of enlarging the region of the target while performing dragging and changing the second threshold value on the periphery of the destination of the dragging. In this case, the receiving unit 210 receives designation of a region to be enlarged. The second display control unit 208 changes the color of a region to be enlarged to the predetermined color. The fixing unit 212 fixes the threshold value of the region to be enlarged as the second threshold value (250) at the time of designation.

Figure 6F:
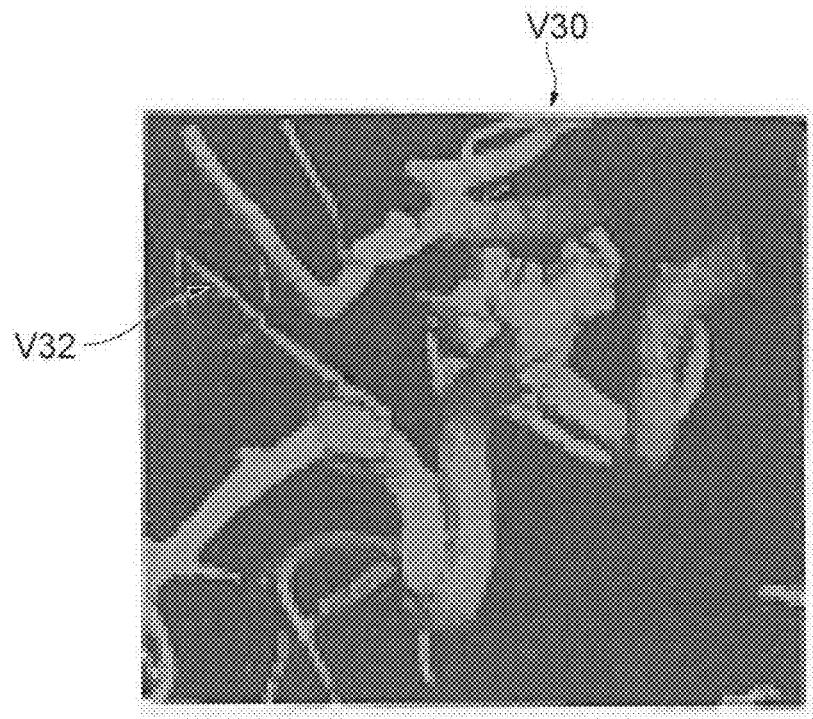
FIG. 6F is a view for describing the designation processing of a target region (stage 6).
Figure 6G:
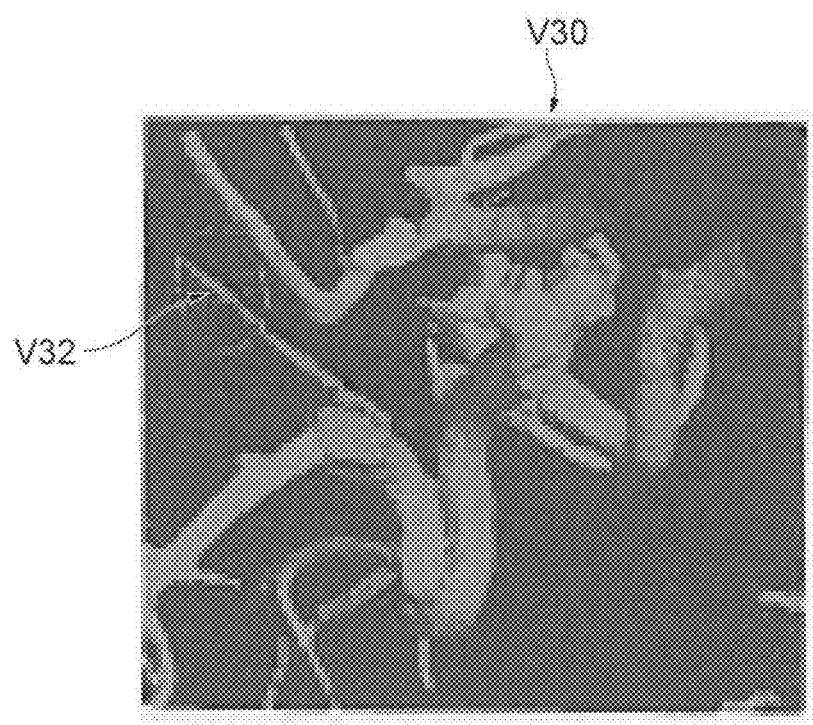
FIG. 6G is a view for describing the designation processing of a target region (stage 7).

In FIGS. 6F and 6G, the user appropriately changes the second threshold value, continues a dragging operation, and enlarges the predetermined region intended to be extracted. In addition, for example, the user is capable of changing the radius of the tip of the brush displayed in the screen by pressing down the upward arrow key or the downward arrow key in the keyboard.

For example, it is possible to continuously perform region enlargement processing in the dragging operation described above until the target region of the extraction target is able to be extracted or until clutter is deleted.

Figure 6H:
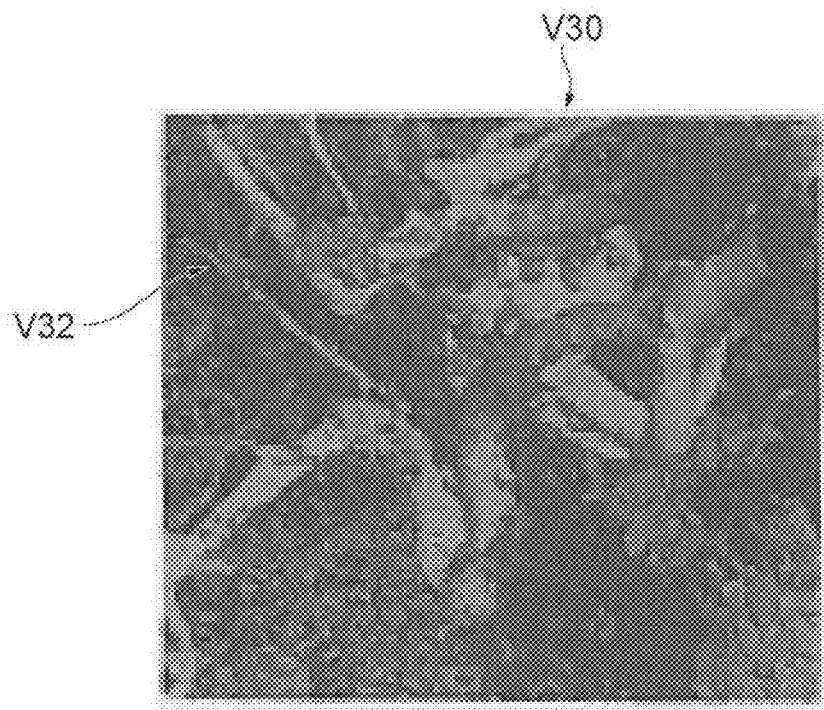
FIG. 6H is a view for describing the designation processing of a target region (stage 8).

In FIG. 6H, the user causes the first threshold value to return to 250 again by using the slider S10. In this case, the region which has already been changed to the predetermined color in able to be discriminated from other regions without being affected by the change of the first threshold value.

<Data Expression>

Data expression for a three-dimensional image in the present invention will be described. Each of points in a three-dimensional image holds volume data having a fixed intensity value through each step of the processing of the present invention. Moreover, each of the points holds a threshold value which is able to be changed by the user. In addition, each of the points holds status data indicating either of "fixed" or "free". In the beginning, the status is "free", but points in the region designated (painted) by the user are changed to "fixed".

A standard marching cube algorithm is applied in order to extract an isosurface. First, temporary volume data is calculated by subtracting the threshold value from the volume data. Subsequently, the marching cube algorithm is applied, and then the threshold value becomes zero. Accordingly, an isosurface is extracted.

Figure 7:
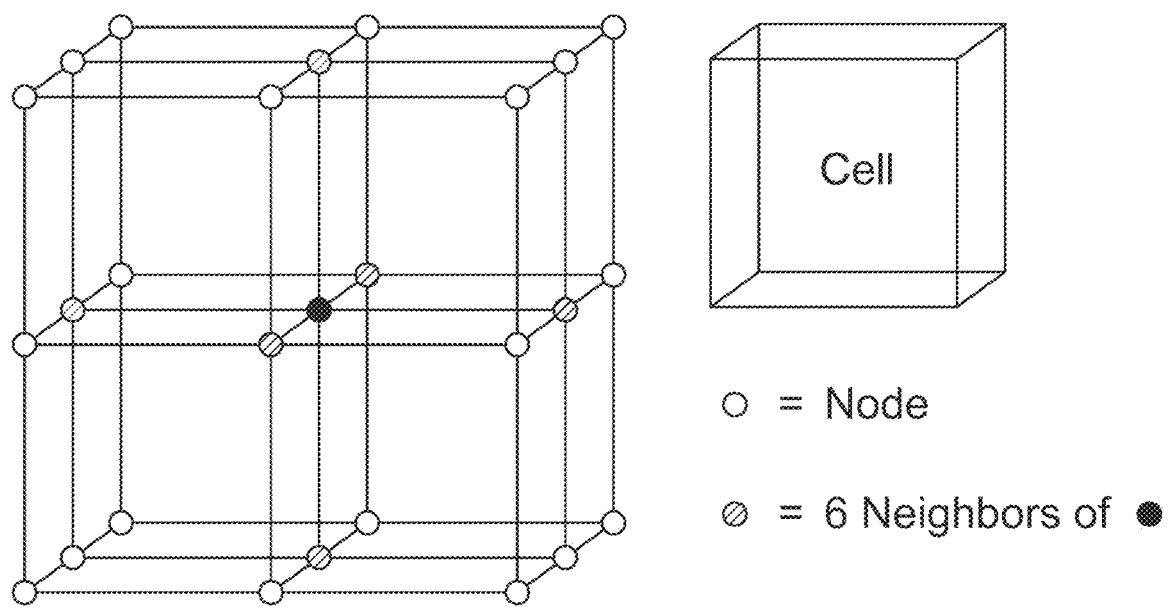
FIG. 7 is a view illustrating an example of data expression according to the embodiment.

Hereinafter, each of the points in a three-dimensional image will be referred to as a node. FIG. 7 is a view illustrating an example of data expression according to the embodiment. In the example illustrated in FIG. 7, each node is associated with the intensity value, the threshold value, and the status data. The marching cube algorithm generates a meshed surface on an inner side of a cell surrounded by eight neighbor nodes. If nodes as many as X×Y×Z are present, cells as many as (X−1)×(Y−1)×(Z−1) are present in total. Each node has six neighbor nodes.

As described above, in the embodiment, since the threshold value is set to each node, an image in the entirety has a threshold value field. In the embodiment, in a case where all of the threshold values of the voxels within the threshold value field are changed, the changing unit 202 performs the change by using the slider S10 illustrated in FIG. 3. In a case where the threshold values on the periphery of the destination of the dragging are changed, the changing unit 202 performs the change by receiving the predetermined operation during dragging. In addition, the threshold value field includes a region designated by the user, and the threshold values of the voxels within the region are fixed. The fixed threshold values are not changed through an overall change of the threshold value by the changing unit 202.

<Operation of Tools>

In the filling tool of the button B24 illustrated in FIG. 3, the user clicks the predetermined position on the screen. The image processing device 10 applies a pick operation in order to find a surface of a current isosurface which appears on the screen. The image processing device 10 discriminates a cell including the surface and specifies eight nodes around the cell. If the intensity of the node is higher than the threshold value, the image processing device 10 causes the node to be in the fixed status. The image processing device 10 causes six neighbor nodes of the node to be in the fixed status.

Subsequently, in the brushing tool, the user drags a mouse cursor, and the image processing device 10 applies a pick operation in order to find a foreground cell below the mouse cursor. The image processing device 10 causes the tip of the brush to be disposed in the middle of the picked cell and specifies a node having a distance from the brush tip to the node is shorter than the radius of the brush.

The image processing device 10 sets the threshold value of the specified node as the second threshold value of the brush. If the threshold value set to the node is lower than the intensity, the image processing device 10 changes the status of the node to the fixed status.

As the brushing operation starts, the image processing device 10 sets the second threshold value of the brush to the threshold value of the foreground node around the picked cell. If there is a plurality of foreground nodes around the cell, the smallest node is used. As described above, the user is capable of changing the second threshold value of the brush through the predetermined operation.

Subsequently, although it is not illustrated in FIG. 3, a cleaning tool will be described. The cleaning tool is a tool for clustering a fixed node. The image processing device 10 measures the diameter of each cluster of which the maximum value between a pair of nodes within a cluster is defined. If the diameter is smaller than the threshold value set in advance, the image processing device 10 sets the status of the node within the cluster to the "free" status.

<Protection Processing>

Subsequently, protection processing for nodes the will be described. First, as a prior condition, if the threshold value is changed by using the slider S10 illustrated in FIG. 3, the image processing device 10 sets changed threshold values to all of the nodes of which the status is "free". In this case, a problem illustrated in FIG. 8 is caused.

Figure 8:
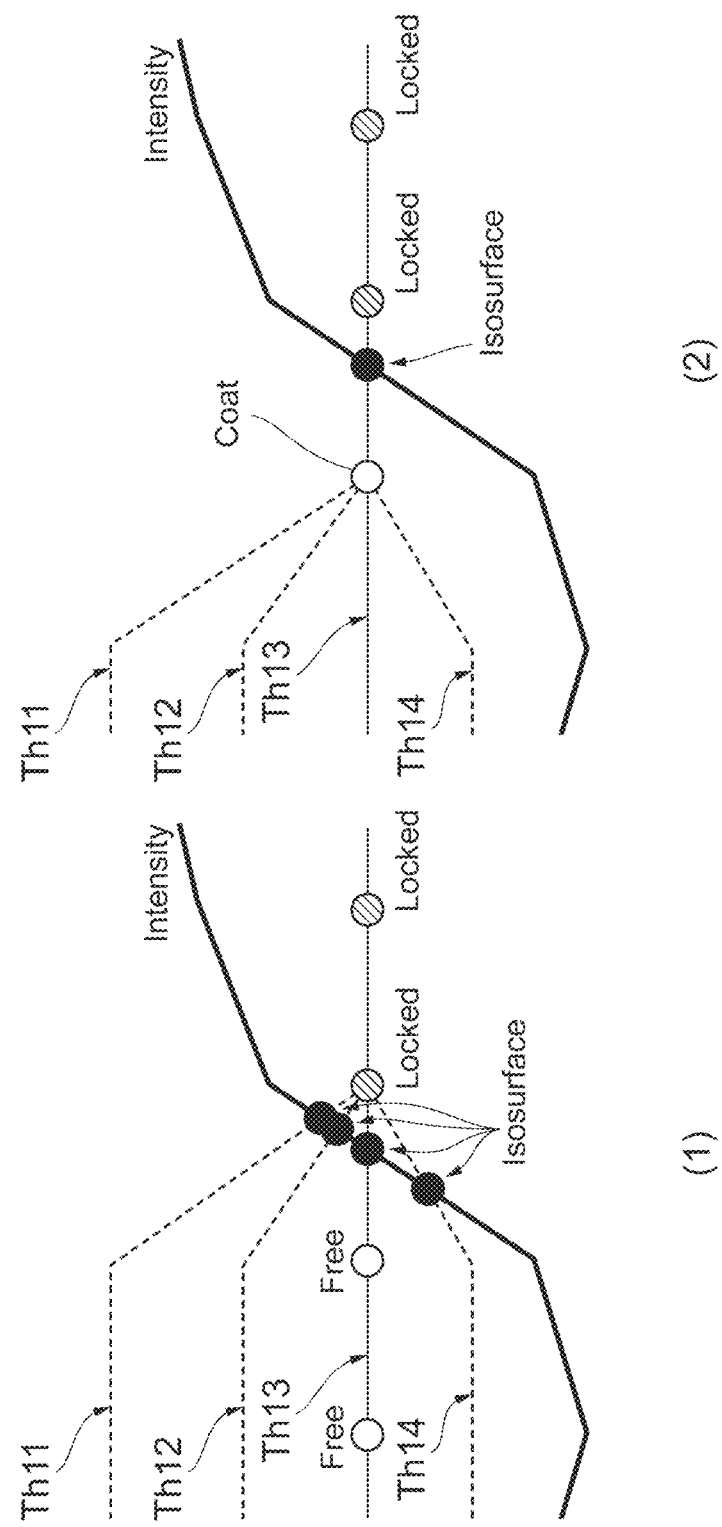
FIG. 8 is a view for describing a problem entailed in a change of a threshold value.

FIG. 8 is a view for describing a problem entailed in a change of a threshold value. In the example illustrated in (1) of FIG. 8, the state of the painted isosurface changes due to a change of the threshold value. In (1) of FIG. 8, as the threshold value changes from Th11 to Th14, the intensity of the isosurface decreases. In order to avoid a change of the isosurface supposed to be fixed, as illustrated in (2) of FIG. 8, if a node neighboring the fixed node is a free node, the free node is protected (fixed). Accordingly, even if the threshold value is changed, since the state of the isosurface does not change, it is possible to provide stable displaying of the isosurface.

<False Isosurface>

If a painting interface according to the embodiment is used, the image processing device 10 sometimes generates a false isosurface on the border of the painted region in a case where there is no region of high intensity.

Figure 9:
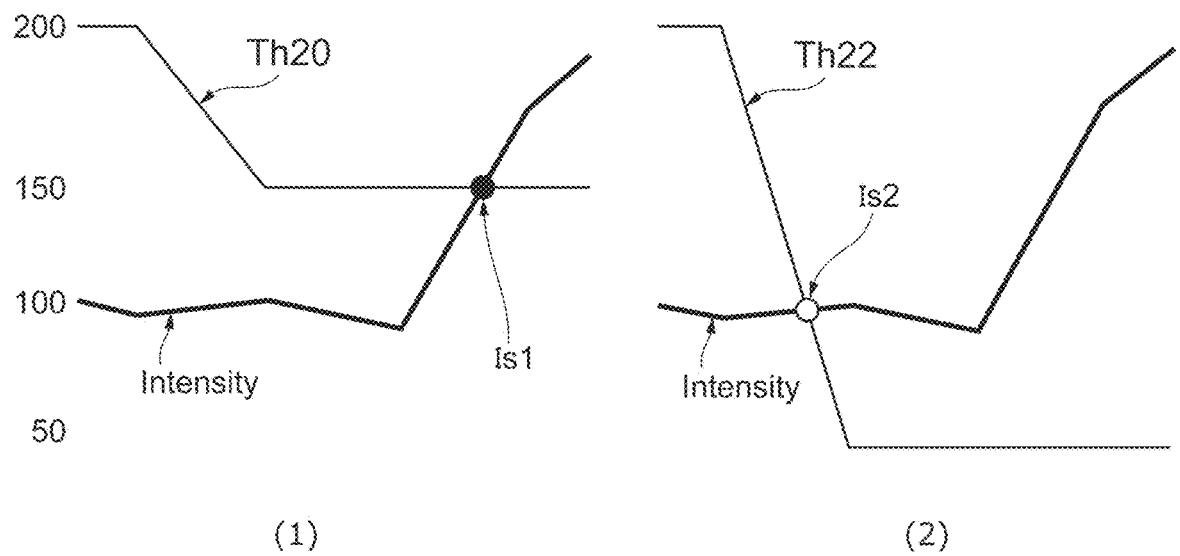
FIG. 9 is a view for describing a false isosurface.

FIG. 9 is a view for describing a false isosurface. The diagram (1) of FIG. 9 illustrates an example in which a proper threshold value is set in order to catch a region including points of high intensity. As illustrated in (1) of FIG. 9, in a case where there are a background region of which the intensity value is 100 and a region of which the intensity value is 200, it is proper to set the threshold value to 150 in order to extract the region of high intensity. Accordingly, a proper isosurface Is1 is displayed.

However, the diagram (2) of FIG. 9 illustrates an example in which an improper threshold value is set and a false isosurface appears. As illustrated in (2) of FIG. 9, in a case where the threshold value is set to 50 and a region of high intensity is painted, a false isosurface Is2 is displayed in the vicinity of the border of the painted region. There is a possibility that the problem will be caused in a case where the gradient of the threshold value is greater than the gradient of the intensity value.

Therefore, the detection unit 214 of the image processing device 10 calculates the downward gradient direction of the intensity value and the normal direction of the isosurface for each of the cells and determines whether or not a predetermined condition based on the directions is satisfied. The predetermined condition denotes that an angle formed by the two directions is equal to or greater than a predetermined angle.

If the predetermined condition is satisfied, the detection unit 214 determines that the isosurface does not properly express the original internal structure and detects the false isosurface. The second display control unit 208 performs controlling such that the false isosurface is displayed in color (for example, green) determined in advance.

In order to further facilitate implementation, the detection unit 214 may use the downward gradient direction of the value which is able to be obtained by subtracting the threshold value from the intensity value, as the normal direction of the isosurface.

Figure 10:
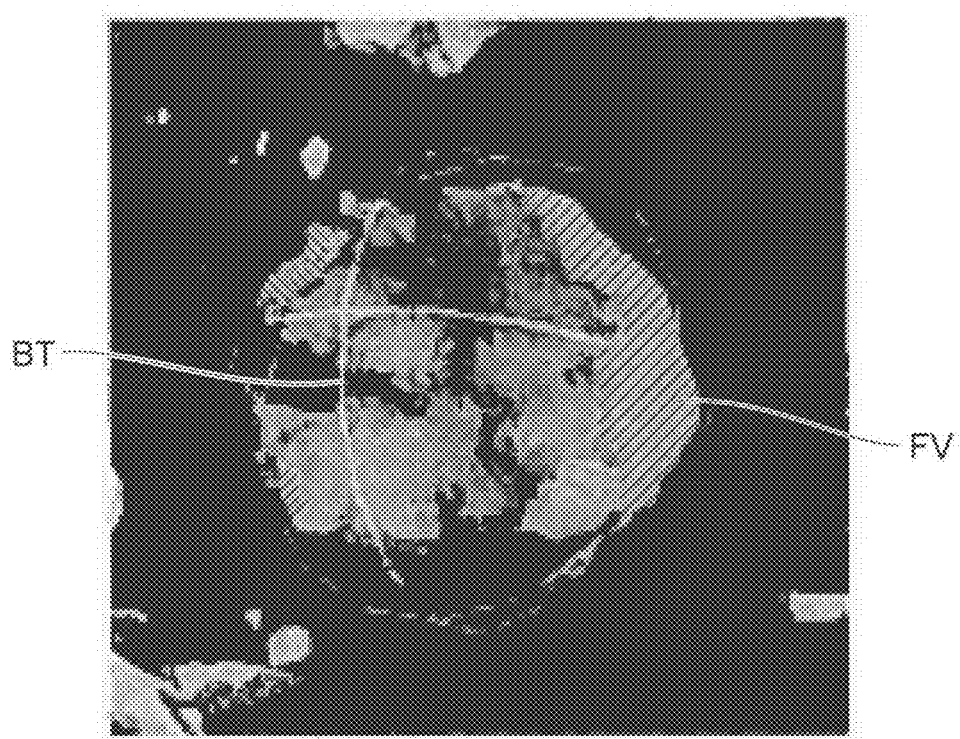
FIG. 10 is a view illustrating an example of a false isosurface.

FIG. 10 is a view illustrating an example of a false isosurface. In the example illustrated in FIG. 10, since the user has lowered the second threshold value set to a brush tip BT, a false isosurface FV appears on the border of the brush tip BT. The detection unit 214 extracts the false isosurface FV in the above-described method and enables false isosurface FV to be discriminated (oblique lines in the example illustrated in FIG. 10). The detection unit 214 detects a region in which the downward gradient direction of the threshold value and the normal direction of the isosurface are opposite to each other, as the false isosurface FV.

Accordingly, the user is capable of performing a change such that the second threshold value set to the brush tip BT increases and the false isosurface FV is deleted.

Figure 11:
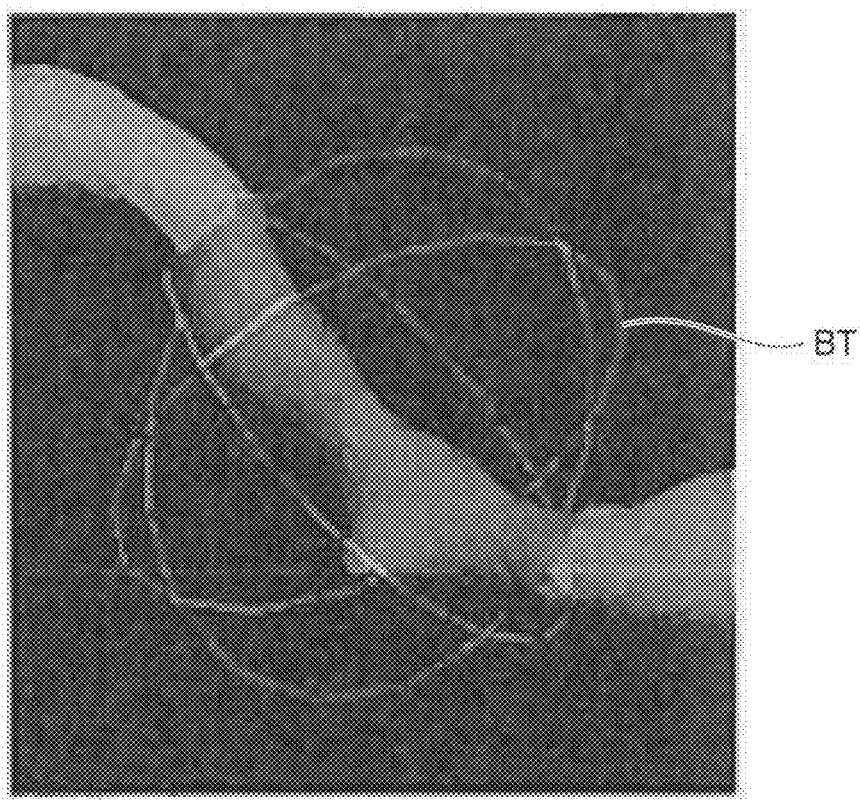
FIG. 11 is a view illustrating an example of a normal isosurface.

FIG. 11 is a view illustrating an example of a normal isosurface. In the example illustrated in FIG. 11, since the gradient direction of the threshold value is substantially orthogonal to the normal direction of the isosurface, the isosurface on the border of the brush is not detected as the false isosurface.

<Operation>

Figure 12:
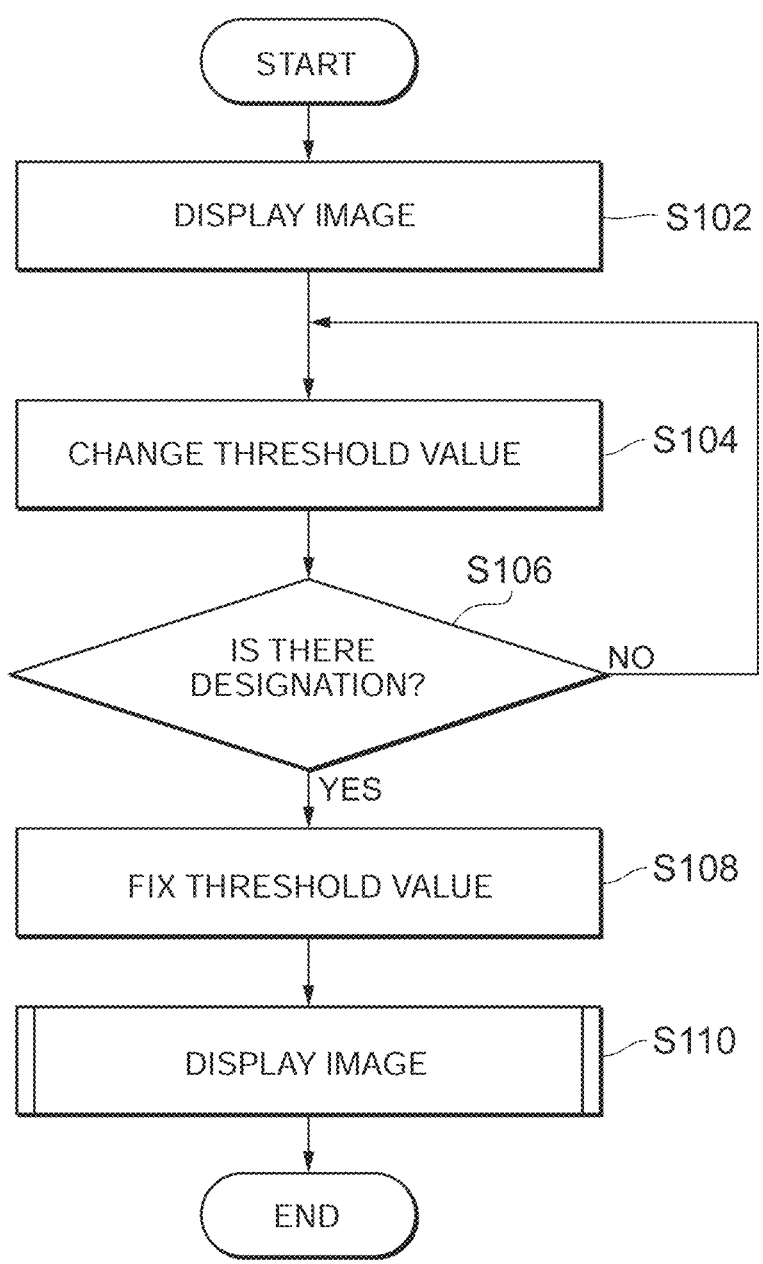
FIG. 12 is a flow chart illustrating an example of target extraction processing according to the embodiment.

Subsequently, an operation of the image processing device 10 will be described. FIG. 12 is a flow chart illustrating an example of target extraction processing according to the embodiment. The processing illustrated in FIG. 12 is executed in a case where the application according to the embodiment is executed and an image is selected.

In Step S102, the first display control unit 206 performs controlling such that the display device 114 displays points including an intensity value equal to or greater than the threshold value of default. For example, the threshold value of default is zero.

In Step S104, the changing unit 202 changes the threshold value of the intensity value of each of the points in an image. For example, the first threshold value is changed by the user operating the knob portion of the slider S10 illustrated in FIG. 3. In this case, the first display control unit 206 controls displaying of the region having points including intensity equal to or greater than the first threshold value every time the first threshold value is changed by the changing unit 202.

In Step S106, the receiving unit 210 determines whether or not designation of the predetermined region of the extraction target is received. For example, the receiving unit 210 receives designation of the interlink region in a case where the button B24 illustrated in FIG. 3 is pressed down, and then a click in the interlink region is detected. If there is designation (Step S106-YES), the processing proceeds to Step S108. If there is no designation (Step S106-NO), the processing returns to Step S104.

In Step S108, the fixing unit 212 fixes the threshold value of each of the points within the designated interlink region as the threshold value at the time of designation of the region.

In Step S110, the second display control unit 208 controls displaying of points including an intensity value equal to or greater than the threshold value fixed by the fixing unit 212 among the points within the predetermined region, and points including an intensity value equal to or greater than the threshold value to be changed by the changing unit 202 among the points outside the predetermined region, in a case where there is one or the plurality of designated interlink regions within the image. In addition, in order to enhance discrimination properties, the second display control unit 208 may change the color of the designated region to the predetermined color. In Step S110, detection processing of the false isosurface may be performed.

In addition, after Step S110, the above-described brushing processing may be performed such that the extraction region of the target is enlarged. In addition, in Step S108, if there is an unfixed node among neighbor nodes of a node of which the threshold value is fixed, the status of the node may be fixed such that the threshold value is fixed. Accordingly, even if the first threshold value is changed by using the slider S10, it is possible to stably display the border of the region of the extraction target.

According to the processing described above, the user is capable of simply designating the extraction target. Therefore, compared to technologies in the related art, it is possible to reduce the time for the extraction processing. Moreover, in the embodiment, since it is possible to improve usability and to be able to perform an intuitive operation by executing designation of the extraction target or enlargement of the region using the painting function, it is possible to further reduce the processing time.

Figure 13:
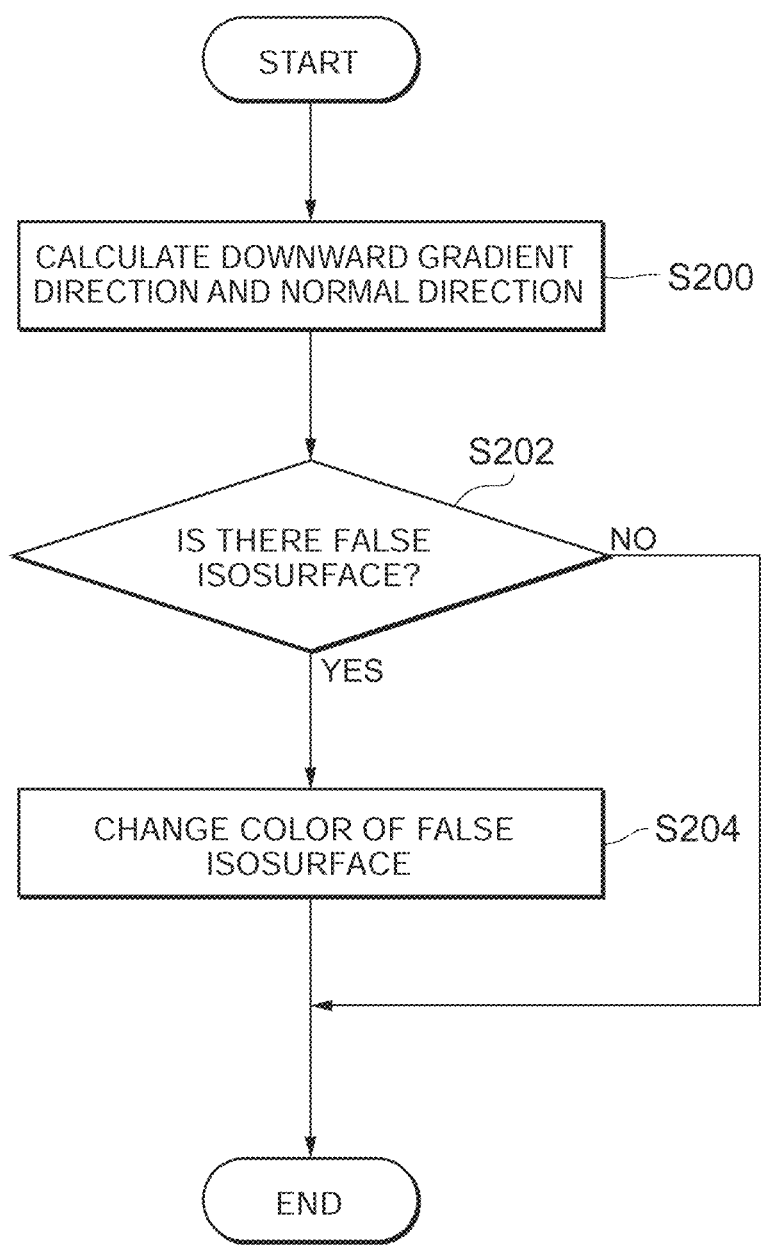
FIG. 13 is a flow chart illustrating an example of processing of detecting a false isosurface according to the embodiment.

FIG. 13 is a flow chart illustrating an example of processing of detecting a false isosurface according to the embodiment. In Step S200 illustrated in FIG. 13, the detection unit 214 calculates the downward gradient direction of the intensity value and the normal direction of the isosurface on the border of the extraction target.

In Step S202, the detection unit 214 determines whether or not the downward gradient direction and the normal direction satisfy the predetermined condition. For example, the predetermined condition denotes that an angle formed by the two directions is equal to or greater than 90 degrees. If the predetermined condition is satisfied (Step S202-YES), it is determined that there is a false isosurface, and the processing proceeds to Step S204. If the predetermined condition is not satisfied (Step S202-NO), it is determined that there is no false isosurface, and the processing ends.

In Step S204, the second display control unit 208 changes the color of the region detected by the detection unit 214 to a color determined in advance. The false isosurface is not limited to being changed in color, the false isosurface need only to be able to be discriminated. The detection processing illustrated in FIG. 13 is also able to be applied to the brushing processing.

According to the processing described above, it is possible to solve the problem of appearance of a false isosurface by using the painting function.

In regard to the program executed by the image processing device 10, as actual hardware, the CPU 102 reads out the program from the ROM 106 and executes the program, one or a plurality of units of the units described above is loaded on the RAM 104, and one or the plurality of units is generated on the RAM 104.

In this manner, the processing described above in the embodiment may be realized as the program to be executed by a computer. It is possible to realize the above-described processing by installing the program through a server or the like and causing the computer to execute the program.

In addition, it is also possible to realize the above-described processing by recording the program in the recording medium 116, causing the computer to read the recording medium 116 in which the program is recorded, and thereby realizing the above-described processing.

As the recording medium 116, it is possible to use various types of recording mediums including a recording medium such as a CD-ROM, a flexible disk, and a magneto-optical disk in which information is optically, electrically, or magnetically recorded; and a semiconductor memory such as a ROM and a flash memory in which information is electrically recorded.

Hereinabove, the embodiment has been described in detail. However, the configuration is not limited to the embodiment described above, and it is possible to make various changes and modifications in addition to the embodiment within the scope disclosed in the aspects.

For example, it is possible to apply the embodiment not only to a three-dimensional image but also to a two-dimensional image. In addition, an image of the application target may be not only an image for medical use but also a scanned image or the like.

Figure 14:
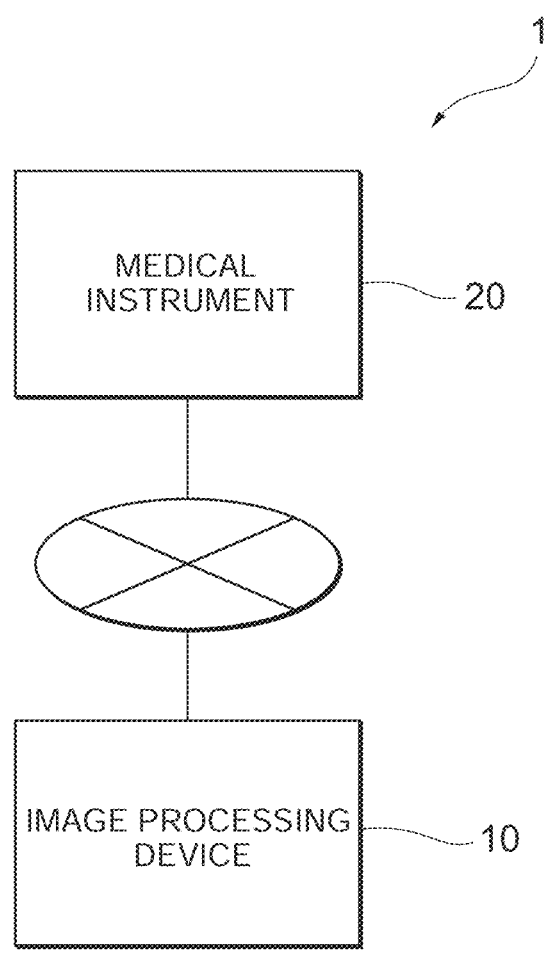
FIG. 14 is a view illustrating a schematic configuration of a medical system according to a modification example.

FIG. 14 is a view illustrating a schematic configuration of a medical system 1 according to a modification example. In the example illustrated in FIG. 14, a medical instrument 20 and the image processing device 10 are connected to each other so as to be able to perform data communication via a network.

The medical instrument 20 is an instrument for acquiring an examination image using CT or MRI. The medical instrument 20 transmits an acquired examination image to the image processing device 10. The image processing device 10 executes the extraction processing of the target described in the embodiment with respect to the acquired examination image.

In FIG. 14, the function of the image processing device 10 may be embedded in the medical instrument 20, and the present invention may be implemented as the medical instrument 20.

REFERENCE SIGNS LIST 10 image processing device
20 medical instrument
102 CPU
104 RAM
106 ROM
202 changing unit
204 display control unit
206 first display control unit
208 second display control unit
210 receiving unit
212 fixing unit
214 detection unit

What is claimed is:

1. An image processing device comprising:
a changing unit that changes a threshold value of intensity of each of points within an image;
a first display control unit that controls displaying of points including an intensity value equal to or greater than the threshold value every time the threshold value is changed by the changing unit;
a receiving unit that receives designation of one or a plurality of predetermined regions within a displayed image based on an operation of a user and that receives an interlink region as designation of the predetermined region in a case where a predetermined position within the interlink region based on the points including an intensity value equal to or greater than the threshold value by the changing unit is designated;
a fixing unit that fixes the threshold value of each of the points within the designated predetermined region as a threshold value by the changing unit at a time of designation of the predetermined region;
a second display control unit that controls, each time the threshold value is changed by the changing unit, displaying of points including an intensity value equal to or greater than the threshold value fixed by the fixing unit, not the threshold value to be changed by the changing unit, among the points within the predetermined region, and points including an intensity value equal to or greater than the threshold value to be changed by the changing unit among the points outside the predetermined region, in a case where there is one or the plurality of predetermined regions within the image, and that controls changing of a color of the interlink region to a predetermined color and displaying of the changed interlink region; and
a detection unit that detects a false isosurface of which a color ought not to be changed to the predetermined color, on a border of the region of which the color is changed to the predetermined color, based on a gradient direction of the intensity of the image and a normal direction of an isosurface of the displayed region.

2. The image processing device according to claim 1, wherein a predetermined operation at a time of a dragging operation having a position within the predetermined region as a starting position enables the changing unit to change the threshold value within a predetermined range from a destination of the dragging operation, and wherein the interlink region includes a trace of the dragging operation, wherein the interlink region is displayed in accordance with a change of the threshold value based on the predetermined operation as the designation of the predetermined region.

3. The image processing device according to claim 1, wherein in a case where there is a neighbor point of which the threshold value is not fixed among points neighboring a point within the predetermined region, the fixing unit fixes the threshold value of the neighbor point.

4. The image processing device according to claim 1, wherein the second display control unit controls changing of the color of the false isosurface detected by the detection unit to a color different from the predetermined color and displaying of the changed false isosurface.

5. An image processing method executed by a computer, the image processing method comprising:
changing a threshold value of intensity of each of points within an image;
controlling displaying of points including an intensity value equal to or greater than the threshold value every time the threshold value is changed;
receiving designation of one or a plurality of predetermined regions within a displayed image based on an operation of a user;
receiving an interlink region as designation of the predetermined region where a predetermined position within the interlink region based on the points including an intensity value equal to or greater than the threshold value is designated;
fixing the threshold value of each of the points within the designated predetermined region as a threshold value at a time of designation of the predetermined region;
controlling, each time the threshold value is changed, displaying of points including an intensity value equal to or greater than the fixed threshold value among the points within the predetermined region, not the threshold value to be changed, and points including an intensity value equal to or greater than the threshold value to be changed among the points outside the predetermined region, in a case where there is one or the plurality of predetermined regions within the image;
controlling changing of a color of the interlink region to a predetermined color and displaying of the changed interlink region; and
detecting a false isosurface of which a color ought not to be changed to the predetermined color, on a border of the region of which the color is changed to the predetermined color, based on a gradient direction of the intensity of the image and a normal direction of an isosurface of the displayed region.

6. The image processing method according to claim 5, wherein a predetermined operation at a time of a dragging operation having a position within the predetermined region as a starting position enables the changing of the threshold value within a predetermined range from a destination of a dragging performed by the dragging operation.

7. The image processing method according to claim 6, wherein the interlink region includes a trace of the dragging operation.

8. The image processing method according to claim 6, wherein the interlink region is displayed in accordance with a change of the threshold value based on the predetermined operation as the designation of the predetermined region.

9. The image processing method according to claim 5, further comprising:
in response to a neighbor point being determined of which the threshold value is not fixed among points neighboring a point within the predetermined region, fixing the threshold value of the neighbor point.

10. The image processing method according to claim 5, further comprising controlling:
changing of the color of the false isosurface to a color different from the predetermined color, and
displaying of the changed false isosurface.

11. A non-transitory computer-readable medium storing instructions that, when executed by at least one programmable processor, cause the at least one programmable processor to perform operations comprising:
changing a threshold value of intensity of each of points within an image;
controlling displaying of points including an intensity value equal to or greater than the threshold value every time the threshold value is changed;
receiving designation of one or a plurality of predetermined regions within a displayed image based on an operation of a user;
receiving an interlink region as designation of the predetermined region where a predetermined position within the interlink region based on the points including an intensity value equal to or greater than the threshold value is designated;
fixing the threshold value of each of the points within the designated predetermined region as a threshold value at a time of designation of the predetermined region;
controlling, each time the threshold value is changed, displaying of points including an intensity value equal to or greater than the fixed threshold value, not the threshold value to be changed, among the points within the predetermined region, and points including an intensity value equal to or greater than the threshold value to be changed among the points outside the predetermined region, in a case where there is one or the plurality of predetermined regions within the image;
controlling changing of a color of the interlink region to a predetermined color and displaying of the changed interlink region; and
detecting a false isosurface of which a color ought not to be changed to the predetermined color, on a border of the region of which the color is changed to the predetermined color, based on a gradient direction of the intensity of the image and a normal direction of an isosurface of the displayed region.

12. The non-transitory computer-readable medium according to claim 11, wherein a predetermined operation at a time of a dragging operation having a position within the predetermined region as a starting position enables the changing of the threshold value within a predetermined range from a destination of a dragging performed by the dragging operation.

13. The non-transitory computer-readable medium according to claim 12, wherein the interlink region includes a trace of the dragging operation.

14. The non-transitory computer-readable medium according to claim 12, wherein the interlink region is displayed in accordance with a change of the threshold value based on the predetermined operation as the designation of the predetermined region.

15. The non-transitory computer-readable medium according to claim 11, further comprising:
in response to a neighbor point being determined of which the threshold value is not fixed among points neighboring a point within the predetermined region, fixing the threshold value of the neighbor point.

16. The non-transitory computer-readable medium according to claim 11, further comprising controlling:
changing of the color of the false isosurface to a color different from the predetermined color, and
displaying of the changed false isosurface.

* * * * *